US008927946B2

(12) United States Patent
Behrens et al.

(10) Patent No.: US 8,927,946 B2
(45) Date of Patent: Jan. 6, 2015

(54) SYSTEM AND METHOD FOR LAYER-WISE PROTON BEAM CURRENT VARIATION

(71) Applicant: Varian Medical Systems Particle Therapy GmbH, Bergisch-Gladbach (DE)

(72) Inventors: Uwe Behrens, Hamburg (DE); Thomas Stephani, Bergisch Gladback (DE)

(73) Assignee: Varian Medical System Particle, Bergisch-Gladbach (DE)

( * ) Notice: Subject to any disclaimer, the term of this patent is extended or adjusted under 35 U.S.C. 154(b) by 0 days.

(21) Appl. No.: 13/887,086

(22) Filed: May 3, 2013

(65) Prior Publication Data
US 2013/0277569 A1    Oct. 24, 2013

Related U.S. Application Data

(63) Continuation of application No. 13/224,773, filed on Sep. 2, 2011, now Pat. No. 8,445,872.

(60) Provisional application No. 61/380,017, filed on Sep. 3, 2010.

(51) Int. Cl.
| | |
|---|---|
| *A61N 5/10* | (2006.01) |
| *H01J 3/14* | (2006.01) |
| *G21K 5/00* | (2006.01) |
| *H05H 13/00* | (2006.01) |
| *H05H 7/02* | (2006.01) |
| *H05H 7/12* | (2006.01) |

(52) U.S. Cl.
CPC .............. *H05H 7/02* (2013.01); *A61N 5/1077* (2013.01); *H05H 2007/122* (2013.01); *A61N 5/10* (2013.01); *A61N 2005/1087* (2013.01); *H05H 13/005* (2013.01); *H05H 2277/11* (2013.01); *H01J 3/14* (2013.01)
USPC ............. 250/492.22; 250/492.23; 250/492.1; 250/492.3; 315/502; 378/65

(58) Field of Classification Search
USPC ................. 250/396 R, 492.1, 492.3, 492.21, 250/492.22, 492.23, 505; 315/500, 502; 378/65
See application file for complete search history.

(56) References Cited

U.S. PATENT DOCUMENTS

| | | | |
|---|---|---|---|
| 6,717,162 B1 | 4/2004 | Jongen | |
| 8,039,822 B2 | 10/2011 | Rietzel | |

(Continued)

OTHER PUBLICATIONS

Timmer, et al. "Automated Cyclotron Tuning Using Beam Phase Measurements." Nuclear Instruments and Method in Physics Research Dec. 1, 2006 vol. 568 No. 2 pp. 532-536.

(Continued)

*Primary Examiner* — Bernard E Souw

(57) ABSTRACT

Systems and methods are provided to perform efficient, automatic adjustment of cyclotron beam currents within a wide range for multiple treatment layers within the same patient and treatment session. In one embodiment, efficient adjustment is achieved by using beam current attenuation by an electrostatic vertical deflector installed in the inner center of the cyclotron. The beam current may, for example, be adjusted by the high voltage applied to the electrostatic vertical deflector. In front of each treatment the attenuation curve of the vertical deflector is recorded. Based on this attenuation curve, the vertical deflector voltage for the needed beam current of each irradiation layer is interpolated. With this procedure the beam current could be automatically adjusted in minimal time over a wide range while maintaining a high level of precision.

30 Claims, 6 Drawing Sheets

(56) References Cited

U.S. PATENT DOCUMENTS

| | | | |
|---|---|---|---|
| 8,440,987 B2* | 5/2013 | Stephani et al. | 250/492.22 |
| 8,445,872 B2* | 5/2013 | Behrens et al. | 250/492.22 |
| 2009/0230327 A1 | 9/2009 | Rietzel | |
| 2009/0236545 A1 | 9/2009 | Timmer | |
| 2012/0056099 A1* | 3/2012 | Behrens et al. | 250/396 R |
| 2012/0223246 A1* | 9/2012 | Stephani et al. | 250/396 R |

OTHER PUBLICATIONS

Geisler, et al. "Commissioning of the Accel 250 MEV Proton Cyclotron." Cyclotrons and Their Applications 2007, pp. 9-14.

* cited by examiner

SYSTEM AND METHOD FOR LAYER-WISE PROTON BEAM CURRENT VARIATION

CLAIM OF PRIORITY

This application is a continuation of U.S. patent application Ser. No. 13/224,773, filed Sep. 2, 2011 both claiming the benefit of U.S. Provisional Application No. 61/380,017, filed Sep. 3, 2010, and is also related to co-pending U.S. patent application entitled "SYSTEM AND METHOD FOR AUTOMATED CYCLOTRON PROCEDURES," Ser. No. 13/887,071, filed on the same day herewith and U.S. patent application Ser. No. 13/225,045, filed Sep. 2, 2011. Each of these references are incorporated by reference herein in their entireties and for all purposes.

TECHNICAL BACKGROUND

Radiation therapy (RT) is a popular and efficient method for cancer treatment, where ionizing radiation is used in an attempt to destroy malignant tumor cells or to slow down their growth. RT is often combined with surgery, chemotherapy, or hormone therapy, but may also be used as a primary therapy mode. Radiation therapy is most commonly administered as external beam RT, which typically involves directing beams of radiated particles produced by sources located externally with respect to the patient or subject to the afflicted treatment area. The beam can consist of photons, electrons, protons or other heavy ions. As the beam travels through matter (e.g., the subject), energy from the ionizing radiation is deposited along the path in the surrounding matter. This energy is known as "dose," and is used to measure the efficacy and accuracy of a radiation beam. Malignant cells are damaged along the path of radiation beam during the RT. Unfortunately, the damage from the radiation is not limited to malignant cells and may be incurred by any interceding or adjacent cells. Thus, the dosage of radiation to healthy tissues outside the treatment volume is ideally minimized to avoid being collaterally damaged.

Proton therapy is one type of external beam radiation therapy, and is characterized for using a beam of protons to irradiate diseased tissue. The chief advantage of proton therapy over other particle-based therapies is the ability to administer treatment dosages three dimensionally, by specifying the depth (i.e., penetration) of applied radiation, thereby limiting the inadvertent exposure of untargeted cells to the potentially harmful radiation. This enables proton therapy treatments to more precisely localize the radiation dosage when compared with other types of external beam radiotherapy. During proton therapy treatment, a particle accelerator, such as a cyclotron, is used to generate a beam of protons from an internal ion source located in the center of the cyclotron. Typically, a cyclotron is located in a location remote from the target treatment room. The generated protons are directed, via magnets, through a series of interconnecting tubes (called the beamline), and applied to a subject in a target treatment room.

Generally speaking, cyclotrons generate a proton beam at a fixed energy for the duration of a proton therapy treatment. During typical proton radiation treatments however, irradiating a tumor often requires irradiating an entire volume (a tumor, for example) at different depths within a patient or treatment subject. These depths, which may be referred to in discrete units as layers, naturally correspond to different "optimal" energy levels. Since cyclotrons operate only at a fixed energy during a treatment session, irradiating different depths can become problematic. Conventional methods for irradiating a volume are performed by applying a single beam current, and begin by targeting the furthest depth within a patient or subject. For differing depths, a component (such as a carbon filter or "degrader") is inserted into the path of the extracted beam at some distance from the cyclotron. The degrader material reduces the speed of the particles (and thereby the beam energy). Every time the proton beam's energy is changed this results in a new "layer" within the patient or target receiving treatment.

However, the degrader material also reduces the density and number of particles comprising the beam (e.g., the "beam intensity") that continues past the degrader. In order to achieve proper dose rates for each layer, this may be compensated by increasing the beam intensity that the cyclotron delivers to the degrader input. Unfortunately, using conventional techniques the change of beam intensity within a cyclotron can take a significant amount of time.

As a result, proton therapy according to conventional operating techniques is generally limited to relatively simple treatment plans, which even then may require exceptionally and inefficiently long irradiation times. In some cases, if the extracted beam current must be frequently varied according to a multiplicity of layers requiring treatment for example, new, practically separate treatment plans would need to be devised which would likely lead to even more delays and inefficiencies. Moreover, due to the complexity of the underlying machines, their operating and maintenance procedures, and the gravity of the corresponding medical procedures, highly trained and skilled operators are needed to perform the calculations and actions necessary to make adjustments to a proton beam current. Naturally, this can result in further inefficiency, delays or even potential hazards if qualified operators are not available.

SUMMARY

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

To overcome the difficulties inherent in traditional cyclotron beam adjustment methods, new techniques for automating these procedures are herein provided. According to one aspect of the invention, a system and methods are provided to perform an efficient adjustment of cyclotron beam currents within a wide range for each treatment layer. In one embodiment, efficient adjustment is achieved by using beam current attenuation by a beam path modulator (such as an electrostatic vertical deflector) installed in the inner center of the cyclotron. The beam current may, for example, be adjusted by applying a high voltage to the electrostatic vertical deflector. The protons will be deflected by the electrical field (generated by the applied voltage) to a vertical collimator. Due to the applied voltage, only a dedicated amount of protons will pass the vertical deflector system. At the beginning of each treatment the attenuation curve of the vertical deflector is recorded. Based on this attenuation curve, the vertical deflector voltage for the needed beam current of each irradiation layer is interpolated. With this procedure, the beam current could be automatically adjusted in minimal time over a wide range while maintaining a high level of precision.

According to one embodiment, a proton radiation treatment is prepared by first setting the maximum beam current to reach the nearest desired depth within the patient (e.g., by proper positioning of moveable phase slits in the cyclotron), subsequently, the beam current is attenuated by adjusting the voltage of an electrostatic vertical deflector to acquire a plurality of data points, thereby generating an interpolation table containing vertical deflector voltages versus resulting extracted beam currents. Using this interpolation table the appropriate vertical deflector settings are determined from the desired beam current setpoints, and adjustment of the extracted beam current can be performed automatically and rapidly, thereby advantageously extending the ability to provide more complex treatment plans while drastically reducing the overall irradiation time.

The maximum beam current for each patient treatment is adjusted by means of two movable phase slits based on an automatically generated look-up table. Beam current adjustment starts by setting the slit widths to defined values. The slits are then opened and allow a precise tuning of the maximal beam current in the range between for example 1 nA to 800 nA. After the adjustment of the phase slits the dependency of the beam current on the voltage of the vertical deflector is recorded. According to some embodiments, the complete sequence can take approximately twenty seconds. Based on this suppression curve, the beam current can be subsequently changed within milliseconds over a wide dynamic range by changing the voltage setting of the vertical deflector during the irradiation.

BRIEF DESCRIPTION OF DRAWINGS

The accompanying drawings, which are incorporated in and form a part of this specification, illustrate embodiments of the invention and, together with the description, serve to explain the principles of the invention.

DETAILED DESCRIPTION

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, and components, have not been described in detail as not to unnecessarily obscure aspects and features of the subject matter.

Figure 6:
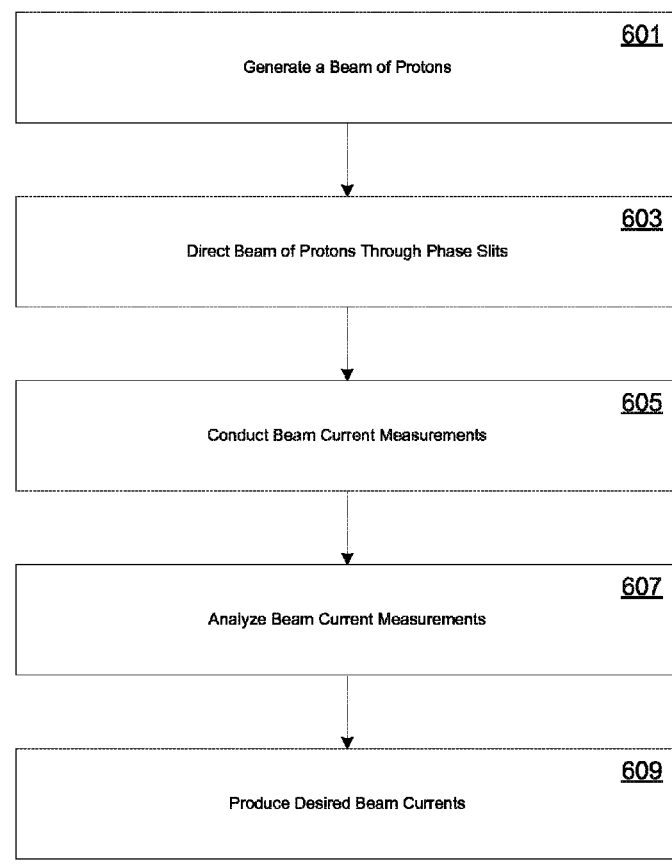
FIG. 6 depicts a flowchart of a method of automatically generating multiple extracted beam currents in an exemplary proton accelerator, in accordance with embodiments of the claimed subject matter.

Portions of the detailed description that follows are presented and discussed in terms of a method. Although steps and sequencing thereof are disclosed in figures herein (e.g., FIG. 6) describing the operations of this method, such steps and sequencing are exemplary. Embodiments are well suited to performing various other steps or variations of the steps recited in the flowchart of the figure herein, and in a sequence other than that depicted and described herein.

Exemplary Proton Accelerator

Figure 1:
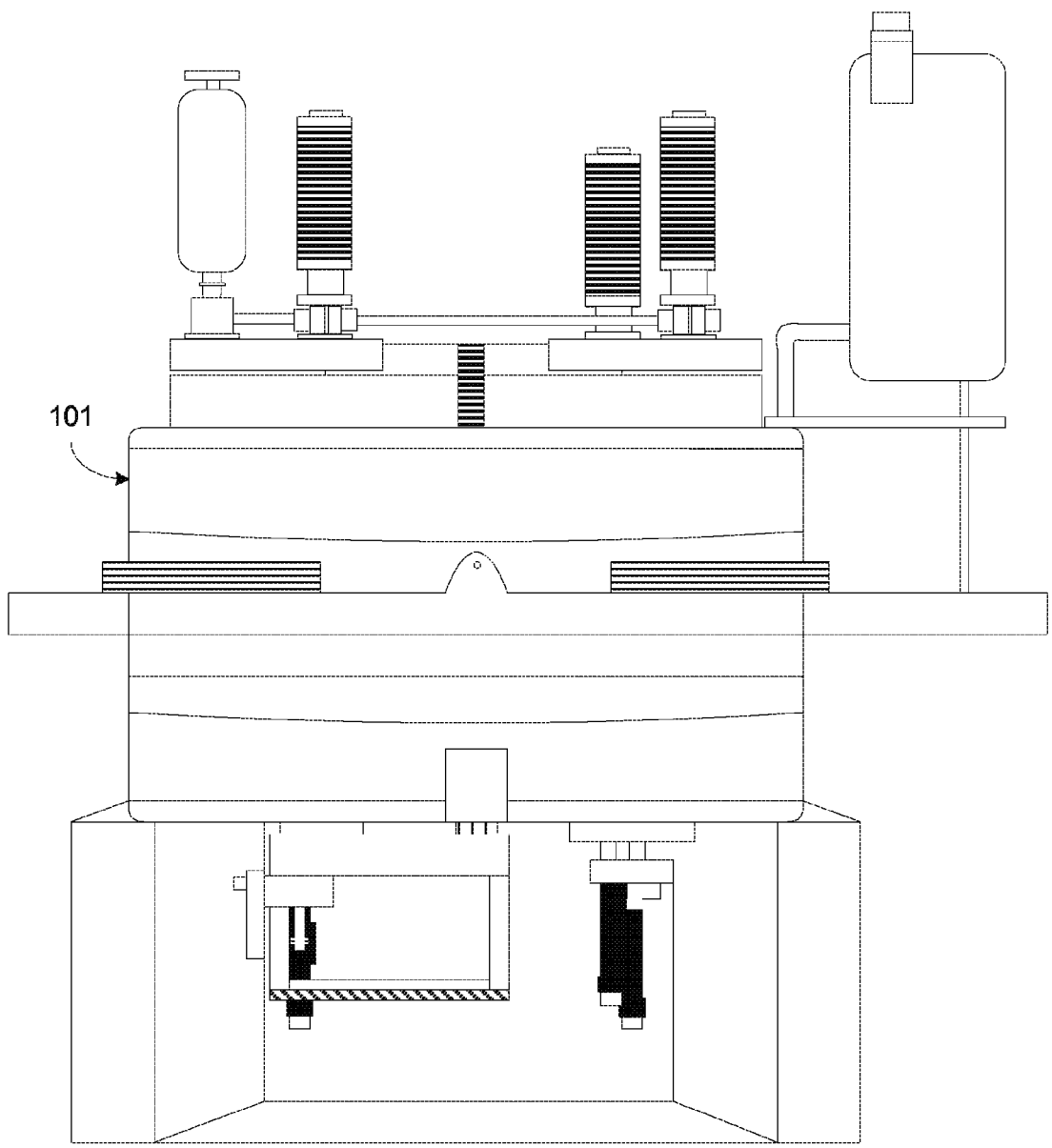
FIG. 1 depicts a diagram of an exemplary proton accelerator, in accordance with various embodiments of the claimed subject matter.

With reference now to FIG. 1, an illustration of an exemplary proton accelerator 100 is depicted, in accordance with one embodiment. In one configuration, the proton accelerator 100 may be implemented as a cyclotron. In further embodiments, the cyclotron may be, for example, a compact four sector isochronous cyclotron incorporating a superconducting main coil. As depicted, the superconducting main coil may be housed in a central chamber 101, in which particles of a generated proton beam from an ion source are accelerated on radially increasing trajectories. In an exemplary configuration, the cyclotron operates with a beam energy of 250 MeV, and capable of generating a maximum beam current of about 800 nA and the typical extraction efficiency is 80%.

Figure 2:
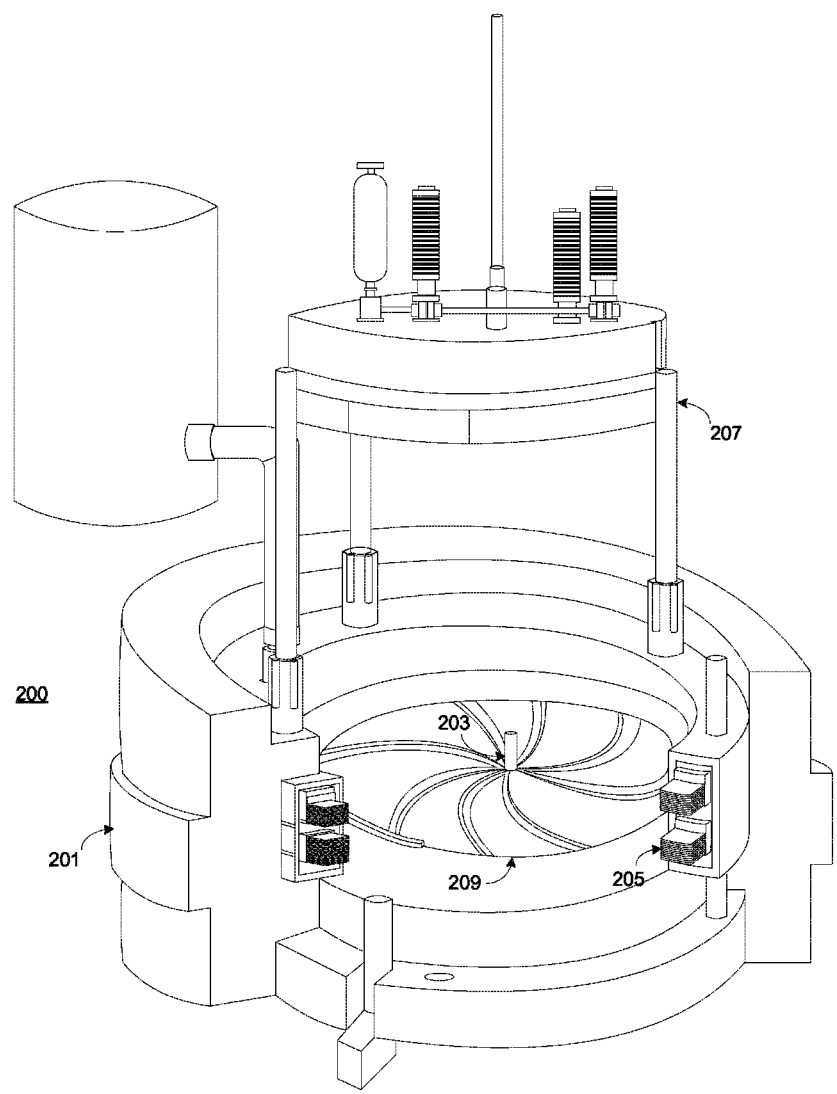
FIG. 2 depicts an expanded-view diagram of an exemplary proton accelerator, in accordance with various embodiments of the claimed subject matter.

With reference now to FIG. 2, an illustration of an expanded-view diagram of an exemplary proton accelerator 200, in accordance with various embodiments of the claimed subject matter. The exemplary proton accelerator 200 may, for example, be implemented as the cyclotron described above with reference to FIG. 1. As depicted, FIG. 2 depicts the upper portion of a cyclotron 200 with a raised top 207 (typical during the performance of maintenance, for example). A beam of protons is generated in a central chamber 209 by an ion source 203, and radially accelerated by electrical fields of a radio frequency (RF) driven sub-system and guided to the extraction radius in a spiral form by the magnetic field induced by the superconducting main coil (depicted, in part, as 205).

Figure 3:
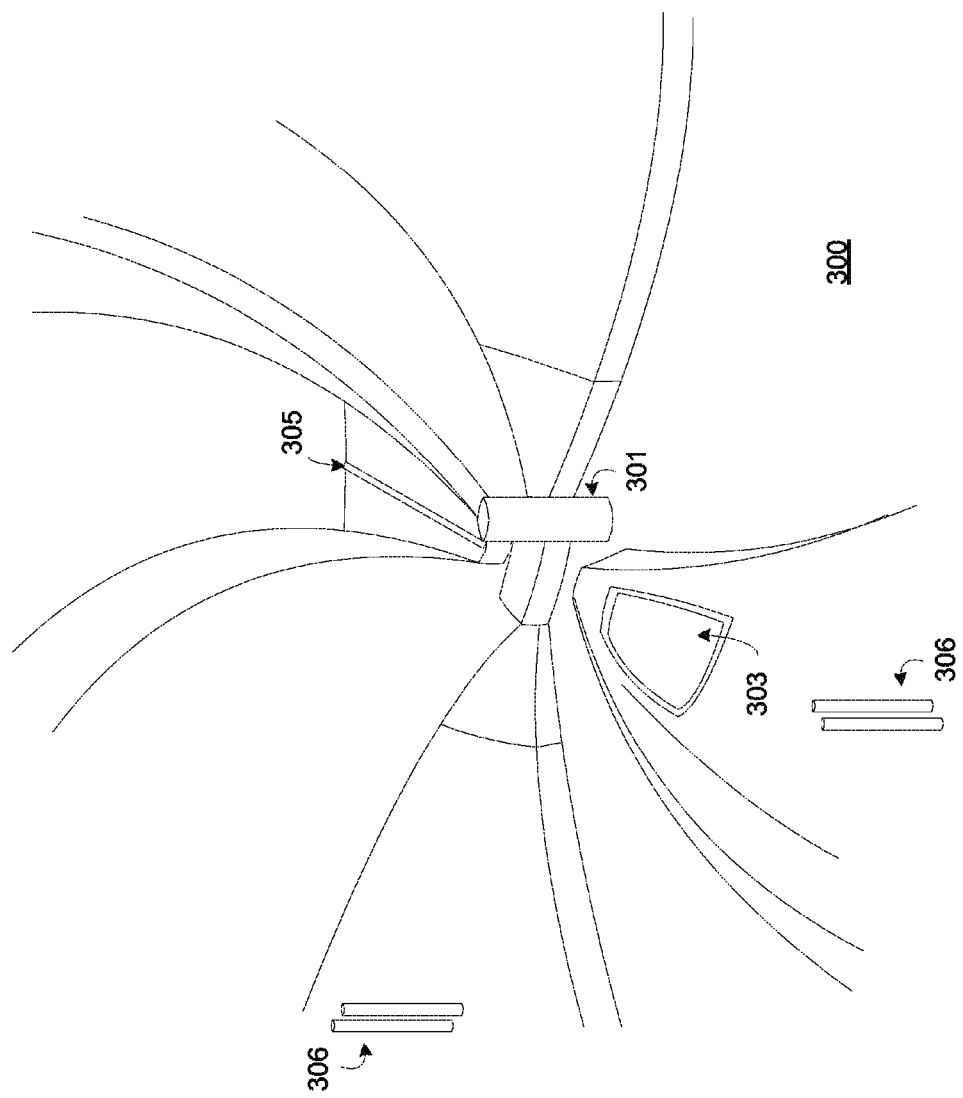
FIG. 3 depicts an illustration of the central region of an exemplary proton accelerator, in accordance with various embodiments of the claimed subject matter.

FIG. 3 depicts a close-up illustration of a portion of the central chamber 300 (e.g., central chamber 209) in an exemplary proton accelerator (e.g., cyclotron 100 and 200), in accordance with various embodiments of the claimed subject matter. The portion of the central chamber 300 depicted in FIG. 3 includes an internal ion source 301, an beam path modulator (e.g., electrostatic vertical deflector plate 303 and vertical collimator plate 305). According to one embodiment, during a proton therapy treatment session, a proton beam emanates as a stream or bursts of protons from the ion source 301, the stream of protons is accelerated by electrical fields of the RF system and guided to the extraction radius in a spiral form via the magnetic field in the central chamber 300 produced by magnetic coils (e.g., magnetic coils 205).

The produced proton beam is threaded through one or more beam current modulators (e.g., phase slits 306), resulting in an extracted proton beam having a corresponding beam current. As presented, the phase slits 306 include apertures through which the proton beam travels. In one embodiment, the size of the aperture of a phase slit 306 is of sufficient size to allow a generated proton beam to traverse completely unimpeded. According to alternate embodiments, the size of the aperture of the phase slit 306 is less than that of a complete proton beam, such that at least a portion of any generated proton beam is absorbed by the material of the phase slit 306 when the proton beam is travelling through the aperture.

Tuning the proton beam (and by extension, the beam current of an extracted beam) may be performed by producing a voltage in the electrostatic vertical deflector 303, thereby producing an electric field. The properties imparted by the electric field affect the particles comprised in the beam of protons, and is capable of influencing the trajectory of the produced proton beam. A stronger electric field produces a greater influence, and thus, the proton beam is capable of being aimed to the extent that the trajectory of the proton beam is at least partially directed into (and thus, intercepted by) the vertical collimator 305 by running varying voltages through the electrostatic vertical deflector 303. For example, in one embodiment, a maximum beam current may correspond to little or no voltage in the electrostatic vertical deflector 303, thereby leaving most if not all of the produced beam through the aperture unimpeded.

The transmitted beam of the vertical deflector and collimator systems will be guided to the phase slits 306. According to one embodiment, the opening widths of the phase slits are variable and a portion of the proton beam could be stopped by this measure. If the apertures of the phase slits are completely open, the transmitted beam by the vertical deflector and collimator systems and the extracted beam may have approximately the same beam current (only influenced by the extraction efficiency of the cyclotron). The magnitude of the electric field of the vertical deflector may be controlled by running smaller or larger voltages through the electrostatic vertical deflector 303. The portion of the proton beam that travels through the apertures of the vertical collimator and the phase slits has a decreased beam current with an intensity lowered by an amount which corresponds to the portion of the produced proton beam intercepted by the non-aperture portion of the vertical collimator and the phase slits.

Figure 4:
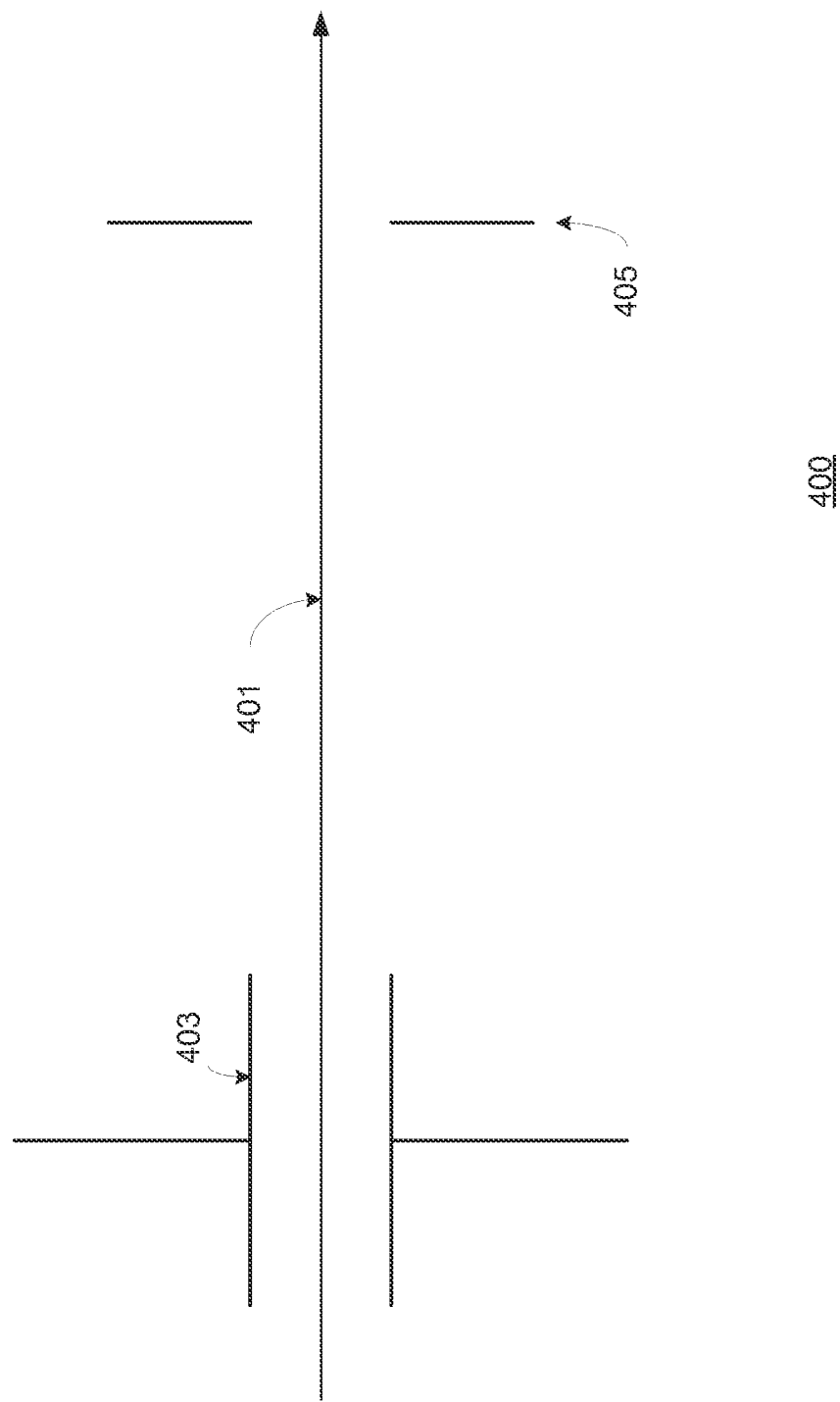
FIG. 4 depicts an illustration of an example non-spiral trajectory without influence from an electric field generated by an electrostatic vertical deflector system in an exemplary proton accelerator, in accordance with embodiments of the claimed subject matter.

With reference now to FIG. 4, an illustration 400 of an example trajectory 401 of a proton beam without being influenced by an electric field generated by a electrostatic vertical deflector 403 in an exemplary proton accelerator is depicted, in accordance with embodiments of the claimed subject matter. As presented in FIG. 4, an electrostatic vertical deflector 403 and a vertical collimator 405 with an aperture are disposed in a cyclotron (e.g., cyclotron 100 and 200). In further embodiments, the electrostatic vertical deflector 403 and vertical collimator 405 are disposed within a central chamber (e.g., central chamber 209) of the cyclotron. A generated proton beam (e.g., emanating from an ion source such as ion source 203) with sample trajectory 401 travels through an area adjacent to an electrostatic vertical deflector 403, and towards (and through) the vertical collimator 405. As shown, with little (or no) influence by an electric field generated by the electrostatic vertical deflector 403, the generated proton beam is able to travel directly through the aperture of the vertical collimator 405 unimpeded, losing little to no beam intensity (and thus, maintaining a consistent beam current) in the process. As presented, the sample trajectory 401 may, for example, correspond to a maximum desired beam current for a proton treatment therapy.

Figure 5:
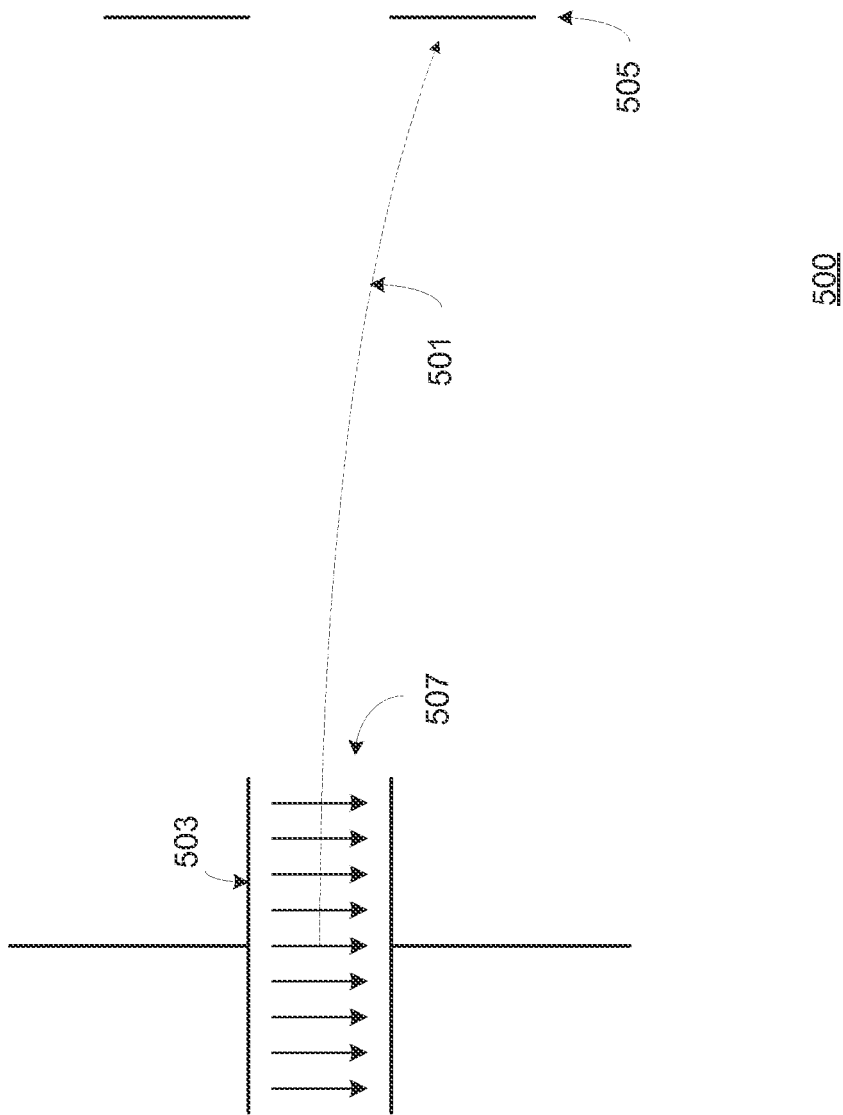
FIG. 5 depicts an illustration of an example non-spiral trajectory influenced by an electric field generated by an electrostatic vertical deflector system in an exemplary proton accelerator, in accordance with embodiments of the claimed subject matter.

Conversely, and with reference now to FIG. 5, an illustration 500 of an example trajectory 501 of a proton beam influenced by an electric field generated by a electrostatic vertical deflector 503 in an exemplary proton accelerator is depicted, in accordance with embodiments of the claimed subject matter. As presented in FIG. 5, the electrostatic vertical deflector 503 and vertical collimator 505 with an aperture and corresponding to their equivalents in FIG. 4 (electrostatic vertical deflector 403 and a vertical collimator 405, respectively) are disposed within a central chamber (e.g., central chamber 209) of a cyclotron (e.g., cyclotron 100 and 200). According to one embodiment, running a voltage through the electrostatic vertical deflector 503 creates an electric field 507. A generated proton beam (e.g., emanating from an ion source such as ion source 203) with sample trajectory 501 travelling through the electric field 507 towards (and through) vertical collimator 505 will be impacted by the properties of the electric field 507. An electric field with sufficient magnitude is capable of altering the trajectory of the proton beam. As shown, with sufficient influence by an electric field generated by the electrostatic vertical deflector 503, the generated proton beam can be directed towards the non-aperture portion of the vertical collimator 505, having the particles of the beam impeded by the non-aperture portion of the vertical collimator 505 being absorbed by the material of the vertical collimator 505, and losing beam intensity proportional to the portion of the beam that was obstructed (and thus, decreasing the beam current) in the process. As presented, the sample trajectory 501 may, for example, correspond to a desired beam current less than the maximum beam current (e.g., shallower "layers" in a target subject) for a proton treatment therapy.

Proton Beam Trajectory Tuning

During medical operation, the control and oversight of a generated proton beam may be completely managed by a higher level control system operating in a computer system (thus not necessitating manual operation). This management may include, for example, the requests for desired beam currents. During operation of the cyclotron, adjustments to the generated beam may be performed to produce varying extracted beams. According to one embodiment, a proton radiation beam is generated at step 601. The generated proton radiation beam may have an initial beam current set to the maximum beam current calculated to reach the needed intensity for the lowest desired depth for a radiation treatment plan (e.g., by proper positioning of moveable phase slits in the cyclotron). The maximum beam current for each treatment is adjusted by means of two movable phase slits (the position and/or aperture size of phase slits may, for example, be calculated by manually or automatically referencing a table of configuration data, for example). Beam current adjustment may begin by setting the phase slit widths to pre-defined values. The slits are then opened to allow passage of the generated beam at step 603, and precise tuning of the beam current (e.g., typically within the range between 1 nA to 800 nA) may be performed by adjusting the positions of the phase slits.

The tuning of the beam current is performed by a multi-step process which begins by measuring extracted beam currents under varying circumstances, performed at step 605. After the adjustment of the phase slits, varying voltages are generated in a vertical deflector, producing electric fields of varying magnitudes. The generated electric fields influence the trajectory of the produced beam traveling through the vertical collimator. For example, if the magnitude of the field is sufficient to affect the trajectory such that a portion of the proton beam's path is obstructed by the non-aperture portion of the vertical collimator, the resultant beam current is attenuated by a corresponding amount. The resulting suppressed beam current is monitored and tracked for varying pre-determined data points (e.g., the radial positions of the phase slits, the voltage in the vertical deflector), and the correspondence of the extracted beam and the voltage of the vertical deflector is measured and recorded (e.g., at a local or remotely located computing device). According to some embodiments, five or more data points (e.g., configurations) may be tracked and monitored for a treatment during the tuning process. In further embodiments, the five or more data points may be distributed in the range between the maximum desired beam current and the minimum desired beam current for a proton treatment therapy session.

The data is then analyzed at step 607 to determine the correspondence between an extracted beam current and a voltage of the vertical deflector required to produce a beam having the extracted beam current (e.g., by extrapolating the data points to approximate a curve). The complete sequence may, according to some embodiments, take up to twenty seconds. Once the data points are analyzed and the appropriate vertical deflector positions are determined, the adjustment of the beam to produce extracted beams with varying beam currents (and thus, intensity) can be performed automatically and rapidly. Based on this plotted curve, the beam current can be subsequently adjusted within milliseconds (e.g., 600 ms), such that the beam currents corresponding to various layers in a treatment plan for a patient—that is, the depths desired within a target subject according to a proton treatment plan—can be generated by determining, on the analyzed suppression curve, the configurations of the electrostatic vertical deflector which correspond to the desired beam currents. Thus, once steps 601-607 are performed, a proton treatment plan comprised of multiple layers in a target patient may be treated with a single generated proton beam by automatically producing varying extracted beams with beam currents corresponding to each of the layers over a wide dynamic range by changing the voltage setting of the vertical deflector to allow efficient, versatile, and adjustable proton radiation treatments.

What is claimed is:

1. A proton therapy system, the proton therapy system comprising:
    a cyclotron, the cyclotron comprising:
        a plurality of sub-systems collectively used to operate the cyclotron, the plurality of sub-systems including at least one sub-system from the group consisting of:
            a magnet sub-system;
            a cooling sub-system;
            a vacuum sub-system;
            a radio frequency sub-system;
            a beam injection sub-system,
        an ion source for producing a proton treatment beam having a beam current;
        a plurality of beam path modulators; and
        a plurality of beam current modulators,
    wherein, the proton treatment beam is directed by at least one of the plurality of beam path modulators such that at least a portion of the proton treatment beam travels through at least one of the plurality of beam current modulators.

2. The system according to claim 1, wherein the plurality of beam path modulators comprises a plurality of electrostatic deflectors.

3. The system according to claim 2, wherein the plurality of beam path modulators comprises a collimator.

4. The system according to claim 1, wherein the plurality of beam current modulators comprises a plurality a moveable slits.

5. The system according to claim 2, wherein the plurality of beam path modulators configurably directs at least a portion of the beam of protons through the plurality of beam current modulators by generating an electric field in the electrostatic-deflector.

6. The system according to claim 5, wherein the plurality of beam path modulators configurably directs at least a portion of the beam of protons through the plurality of beam current modulators by causing a deflection in a trajectory of the beam of protons.

7. The system according to claim 6, wherein the deflection in the trajectory of the beam of protons is caused by the generated electric field in a beam path modulator of the plurality of beam path modulators.

8. The system according to claim 1, wherein a plurality of extracted proton beams is generated from the proton treatment beam and applied to a plurality of target treatment layers disposed in a proton therapy patient.

9. The system according to claim 8, wherein the plurality of target treatment layers comprise target layers with varying depths in the proton therapy patient, and wherein the varying depths correspond to a treatment plan for the proton therapy patient.

10. The system according to claim 8, wherein the plurality of extracted proton beams is generated by attenuating the beam current of the proton treatment beam to correspond to the plurality of target treatment layers.

11. The system according to claim 10, wherein the attenuating the beam current is performed by directing varying portions of the proton treatment beam through the plurality of beam current modulators according to pre-determined measurement data.

12. The system according to claim 11, wherein the pre-determined measurement data comprises a data curve which plots a correspondence between a plurality of extracted beam currents generated from attenuating the beam current of the proton treatment beam and a voltage in the plurality of beam path modulators.

13. The system according to claim 12, wherein a proton therapy treatment comprising a plurality of extracted beam currents corresponding to a plurality of target treatment layers is generated by the system and applied to a proton therapy patient by automatically attenuating the beam current of the proton therapy treatment beam according to measurement data comprised in the data curve.

14. A method for applying proton therapy comprising:
    entering a plurality of power states for a plurality of sub-systems in a cyclotron;
    generating a beam of protons from an ion source comprised in the cyclotron, the beam of protons having a beam current;
    directing, via a plurality of beam path modulators comprised in the cyclotron, the beam of protons through a plurality of beam current modulators;
    conducting a plurality of beam current measurements by performing a plurality of beam current adjustments;
    analyzing the plurality of beam current measurements to determine a plurality of settings for the plurality of beam path modulators; and
    automatically producing a plurality of desired beam currents by adjusting the plurality of beam path modulators to modify the beam current to conform to the plurality of pre-determined configurations.

15. The method according to claim 14, wherein the plurality of pre-determined configurations correspond to a proton therapy treatment plan for a proton therapy patient.

16. The method according to claim 14, wherein the generating, the directing, the conducting, the analyzing and the producing are performed in a cyclotron.

17. The method according to claim 14, wherein the plurality of beam path modulators comprises a plurality of deflector plates.

18. The method according to claim 17, wherein the plurality of beam path modulators comprises a collimator.

19. The method according to claim 14, wherein the plurality of beam current modulators comprises a plurality of moveable slits.

20. The method according to claim 14, wherein the directing the beam of protons through a plurality of beam current modulators is performed by modifying openings of the beam current modulators.

21. The method according to claim 20, wherein automatically producing the plurality of desired beam currents comprises adjusting a configuration of the plurality of beam path modulators to modify the trajectory of the beam of protons such that only a portion of the beam of protons passes through the plurality of beam current modulators.

22. The method according to claim 21, wherein the modifying the trajectory of the beam of protons is performed by generating a voltage in the plurality of beam path modulators.

23. The method according to claim 22, wherein the adjusting a plurality of beam path modulators to modify the trajectory of the beam of protons such that only a portion of the beam of protons passes through the plurality of beam current modulators comprises producing an extracted beam of protons having a beam current corresponding to the portion of the beam of protons which passed through the plurality of beam current modulators.

24. The method according to claim 15, wherein the performing a plurality of beam current adjustments to conduct a plurality of beam current measurements comprises:

configuring the plurality of beam path modulators according to the plurality of pre-determined configurations; and measuring the beam currents of the proton beam produced when the plurality of beam path modulators is configured according to the plurality of pre-determined configurations.

25. The method according to claim 24, wherein the analyzing the plurality of beam current measurements comprises:

measuring beam currents of the proton beam produced when the plurality of beam path modulators is configured according to the plurality of pre-determined configurations; and extrapolating the measured beam currents to generate a curve.

26. The method according to claim 25, wherein the automatically producing the plurality of desired beam currents comprises:

receiving the plurality of desired beam currents, the plurality of desired beam currents corresponding to a plurality of target layers in the proton therapy patient; and determining, on the generated curve, a plurality of beam path modulator configurations that correspond to the plurality of desired beam currents corresponding to the plurality of target layers in the proton therapy patient.

27. The method according to claim 26, wherein the plurality of target layers in a treatment target comprises a plurality of target layers with varying depths disposed in the proton therapy patient.

28. The method according to claim 27, wherein the plurality of target layers with varying depths correspond to a proton therapy plan of the proton therapy patient.

29. The method according to claim 25, wherein the automatically producing the plurality of desired beam currents comprises adjusting the plurality of beam path modulators to conform to the plurality of beam path modulator configurations that correspond to the plurality of desired beam currents.

30. A cyclotron, comprising:

a plurality of sub-systems collectively used to operate the cyclotron, the plurality of sub-systems including at least one sub-system from the group consisting of:
a magnet sub-system;
a cooling sub-system;
a vacuum sub-system;
a radio frequency sub-system;
a beam infection sub-system,
a ion source for producing a beam of protons, the beam of protons having a trajectory and a beam current;
a plurality of electrostatic vertical deflectors with a corresponding vertical collimator for causing a deflection of a trajectory of the beam of protons;
a plurality of phase slits for adjusting a beam current of the beam of protons;
a measuring device for measuring the beam current of a beam of protons produced by the ion source and extracted through the plurality of phase slits,
wherein, the cyclotron is used to perform a proton beam therapy treatment by automatically applying a plurality of beam currents to a target patient, the plurality of beam currents being generated by deflecting, via the plurality of electrostatic vertical deflectors, the trajectory of the beam of protons through the plurality of the vertical collimators and the plurality of phase slits.

* * * * *